US006541198B1

(12) United States Patent
Paulij et al.

(10) Patent No.: US 6,541,198 B1
(45) Date of Patent: Apr. 1, 2003

(54) ANTIBODIES AND OTHER BINDING MOLECULES SPECIFIC FOR HEPATITIS B VIRAL ANTIGENS

(75) Inventors: Wilhelmina Petronella Paulij, Schijndel (NL); Marjolijn Jacqueline Van Kessel-Koens, St. Oederode (NL)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 09/446,787

(22) PCT Filed: Jun. 22, 1998

(86) PCT No.: PCT/EP98/04018

§ 371 (c)(1), (2), (4) Date: Jan. 13, 2000

(87) PCT Pub. No.: WO99/00424

PCT Pub. Date: Jan. 7, 1999

(30) Foreign Application Priority Data

Jun. 27, 1997 (EP) .............................................. 97201968
May 8, 1998 (EP) .............................................. 98201458

(51) Int. Cl.$^7$ ............................ C12Q 1/70; C07K 16/08
(52) U.S. Cl. ......................... 435/5; 435/339; 530/388.3; 436/820
(58) Field of Search ..................... 435/5, 339; 436/820; 530/388.3

(56) References Cited

FOREIGN PATENT DOCUMENTS

EP 0 456 215 A 11/1991
EP 0 521 348 A 1/1993

OTHER PUBLICATIONS

Meisel et al., *Intervirology*, 37(6): 330–339 (1994).
Lee et al., *Biochem. Mol. Biol. Internat.*, 40(6):1077–1085 (1996).
Lee et al., *Biochem. Mol. Biol. Internat.*, 34 (1):159–168 (1994).
Park et al., *Molecules and Cells*, 4(4):413–417 (1994).
Mimms et al., *Virology*, 176(2):604–619 (1990).
Neurath et al., *Molecular Immunology.*, 24(9):975–980 (1987).
Dash et al., *Hepatology*, 13(1):124–142 (1991).

*Primary Examiner*—Donna C. Wortman
(74) *Attorney, Agent, or Firm*—Myers Bigel Sibley & Sajovec, P.A.

(57) ABSTRACT

The present invention relates to antibodies and other binding molecules specific for hepatitis B viral antigens (HBV), peptides comprising epitopes recognized by such molecules, and cell lines capable of producing antibodies. The invention is further concerned with the use of such molecules in diagnosis of HBV. The invention further relates to a method for the diagnosis of hepatitis B, the method comprising contacting the sample suspected to contain hepatitis B particles or antigens with a specific binding molecule according to the invention. The invention further relates to an assay kit for the detection of a hepatitis B particle or antigen, the kit comprising a specific binding molecule of the invention and means for detecting whether the specific binding molecule is bound to a hepatitis B particle or antigen.

12 Claims, No Drawings

ANTIBODIES AND OTHER BINDING MOLECULES SPECIFIC FOR HEPATITIS B VIRAL ANTIGENS

FIELD OF THE INVENTION

The present invention relates to antibodies land other binding molecules specific for hepatitis B viral antigens (HBV), peptides comprising epitopes recognised by such molecules, and cell lines capable of producing antibodies. The invention is further concerned with the use of such molecules in diagnosis of hepatitis B virus (HBV).

BACKGROUND OF THE INVENTION

The virus that causes hepatitis B or serum hepatitis appears to infect only man and chimpanzees. Hepatitis B virus (HBV) infection in humans is widespread.

The hepatitis infection is transmitted by three general mechanisms: (1) by parenteral inoculation of infected blood or body fluids, either in large amounts as in blood transfusions or in minute amounts as through an accidental skin prick; (2) by close family or sexual contact; and (3) by some mothers, who infected during pregnancy, transmit the virus to their new-born children. Under natural conditions, HBV is not highly contagious. Transmission by inhalation occurs rarely, if ever.

The transmission route through contaminated blood or blood products is a major threat to the human health.

Infection with HBV often results in subclinical or acute self-limited liver disease or can result in chronic long-term infection. Chronic HBV infection elicits a spectrum of disease entities ranging from the most severe form of chronic active hepatitis (CAH) to less severe chronic persistent hepatitis (CPH) to the asymptomatic carrier (ASC) state. An array of diagnostic assays have recently been developed to aid the clinician in differentiating hepatitis B virus infections from other forms of viral hepatitis (i.e., HAV, HEV, HCV). However, the ability to distinguish between an acute hepatitis B (AH-B) infection and symptomatic chronic hepatitis B (CH-B) infection is still problematic. This is especially true since CAH and CPH patients often demonstrate a cyclic pattern of hepatitis characterised by acute exacerbations (A.E.) of liver injury alternating with normal liver function.

After infection with HBV, large quantities of the virus and associated particles are present in the serum. During symptomatic phases of infection, both acute and chronic HBV patients have elevated liver enzyme levels, possess the hepatitis B surface antigen (HBsAg) in their serum, and produce antibodies to the nucleocapsid antigen (HBcAg). Antibodies specific for the HBsAg or the hepatitis B e antigen (HBeAg) are not detected. The appearance of antibody to HBsAg is usually not observed until approximately two months following disappearance, of circulating HBsAg. The viral particles present in the serum are known to shed their surface coat exposing the nucleocapsid, known as the core antigen (HBcAg). Antibody production of HBcAg occurs early in the course of the acute phase of HBV infection and can persist for many years, and chronically infected patients can produce high titers of anti-HBc antibodies.

The HBsAg is established as the most important marker of acute or chronic hepatitis B infection, detectable in serum of infected individuals. HBsAg screening of donor blood for example, is essential to avoid transmission of hepatitis B. It is clear that sensitivity is of utmost importance in diagnostic HBV assays.

HBV Surface Antigens (IBsAg)

The HBV surface antigens (HBsAg) are the translational products of a large open reading frame (ORF) that is demarcated into three domains; each of these domains begins with an in-frame ATG codon that is capable of functioning as a translational initiation site. These domains are referred to as Pre-S1, Pre-S2, and S in their respective 5' to 3' order in the gene. Thus, these domains define three polypeptides referred to as S or HBsAg (226 amino acids), Pre-S2+S (281 amino acids), and Pre-S1+Pre-S2+S (289–400 amino acids), also referred to, respectively, as major protein (S-protein), middle protein (M-protein), and large protein (L-protein) (Toillais et al., 1985, Nature, 317, 489–495).

Definition of an HBsAg Subtype

The HBsAg in the viral envelope part of HBV has one well-characterised group specific determinant "a" and two sets of mutually exclusive subtype determinants d/y and w/r. Thus four major subtypes of HBsAg—adw, ayw; adr, and ayr—denote the phenotypes of the virion (Le Bouvier et al., 1975, Amer. J. Med. Sci. 270, 165). Subdivision of "a" specificity into al, a2, a3, and other intermediate specificities which are later redefined as subdeterminants of w (w1–w4) at an international workshop in Paris in 1975 (Courouce et al., 1976, Bibl Hematol, Basel, Karger, vol. 42), the issue of HBsAg subtypes acquired a considerable degree of complexity. These subtypes were ayw1, ayw2, ayw3, ayw4, ayr, adw2, adw4, and adr. With the identification of the q determinant (Magnius et al., 1975, Acta Pathol Micr Scand, 83B, 295–297) the number of subtypes increased from eight to nine, due to the subdivision of the adr subtype into a q-positive and a q-negative category (Courouce-Pauty et al., 1978, Vox Sang, 35, 304–308). Sequencing of complete genomes encoding adw2 and ayw3 subtypes revealed numerous substitutions throughout the genome (Valenzuela et al., 1980, ICN-UCLA, Symposia on Animal Virus Genetics, NY, Ac. Press, pp57–70). A number of these substitutions in the S-gene were claimed to be associated with the expression of d and y specificity (Okamoto et al., 1986, J Gen Virol, 67, 2305–2314). Analysis of reactivity patterns with monoclonal antibodies after chemical modification of HBsAg revealed the importance of Lys 122 for the expression of the d determinant (Peterson et al., 1984, J Immun, 132, 920–927). Later studies on two blood donors carrying surface antigens of compound subtypes adyr and adwr respectively, showed that amino acid substitutions at position 122 and 160 alone explained the expression of d/y and w/r specificity, respectively (Okamoto et al., 1987, J Virol, 61, 3030–3034). Both the d to y and w to r changes were mediated by a shift from Lys to Arg at the corresponding positions. Therefore, major subtypic variations of HBsAg exist.

Definition of an HBsAg Genotype

Sequencing of viral genomes, and comparison has defined four genomic groups of HBV on a divergence of 8% or more of the complete genome, and were designated with A–D (Okamoto et al., 1988, J Gen Virol, 69, 2575–2583). Genomes encoding the subtype adw were found in genomic groups A–C, while the genomes encoding ayw were all found in group D and group B (Sastrosoewignjo et al., 1991, J Gastroenterol Hepatol, 6, 491–498). Genomes encoding both the adr and ayr subtype occurred in genomic group C alongside with adw.

Also two new genotypes of HBV designated with E and F were recently identified (Norder et al., 1994, Virology, 198, 489–503).

Immune Escape Mutants in Relation to Genotypes

Apart from the genetic variability of HBV based on the divergence of HBV strains over long periods of time resulting in geographically related subtypes and genotypes, considerable interest has recently also been focused on two kinds of immune escape mutants. The first of these to be described was a mutation from Trp 28 to a stop codon in the precore sequence, that specifically prevented the expression of HBeAg although leaving that of HBcAg unaffected (Carman et al., 1989, Lancet, ii, 588–591; Brunetto et al., 1991, Proc Natl Acad Sci USA, 88, 4186–4190).

Vaccine escape mutants are described involving the "a" determinant of HBsAg, an important part of which is formed by a loop encompassing amino acid residues 139–147 stabilised by a disulphide bridge between two cysteinic residues at these positions (Waters et al., 1991, Virua Res, 22, 1–12; Stirk et al., 1992, Intervirology, 33, 148–158). One mutation from Gly to Arg at residue 145 of HBsAg was revealed in several vaccinees in Italy (Carman et al., 1990, Lancet, ii, 325–329) and Singapore (Harrison et al., 1991, J Hepatol 13 (suppl 4), S105–107). Another presumed vaccine escape mutation from Lys to Glu at position 141 has only been reported from West Africa (Allison et al., 1993, Abstr. Ixth Int Congr of Virology, Glasgow, pp1–118; Howard et al, 1993, Abstr. Int Symp on Viral Hepatitis and Liver Disease, Tokyo, pp1–75). Interestingly, this mutant has so far only been found in association with the ayw4 subtype. More recently various new mutants were among others described in literature by Brind et al., 1997, J. of Hepatology 26: 228–235; Kohno et al., 1996, J.of gen. virol. 77: 1825–1831; Ni et al., 1995, Res. Virol. 146: 397–407.

From the above it is clear that all sorts of mutations in the HBsAg proteins have to be detected in order to screen blood from donors and other sources.

For example Okomoto et al. (1992) already showed that the affinity between HBsAg mutants and monoclonal anti-HBs antibodies with known epitope specificity was impaired by substitution at amino acid 145 or 126 in the S-region (Okamoto et al., 1992, Pediatric Research 32: 264–268). Substitution of arginine for glycine at amino acid 145 in the yeast vaccine also results in markedly reduced binding by monoclonal antibodies (Waters et al., 1992, J. of clin. invest. 90: 2543–2547). It is further described that the antigenicity of HBsAg is weakened by substitution of amino acid 141 (Earthigesu et al., 1994, J. Gen. Virol. 75: 443–448).

Already various cases of HBsAg positivity which have been missed because of failure of current serological assays to detect some variant forms of the antigen have been described (Suzuki et al., 1995, Int. Hepatology Comm. 4: 121–125; Carman et al., 1995, The Lancet 345: 1406–1407; Jongerius et al., 1997, Ned Tijdschr Geneesk 141 (22) 1128).

Facing the above problems, many diagnostic companies changed their assays by using polyclonal antibodies as capture antibodies instead of using highly specific monoclonal antibodies.

However, drawbacks of using polyclonal antibodies are mainly directed to poor reproducibility, and unknown specificity and sensitivity of the individual antibodies in the total of all antibodies present in the polyclonal serum.

It will therefore always be unknown if newly documented variants will be detected before screening.

Another approach is finding new monoclonal antibodies to the S-region of HBsAg which recognise a well conserved region.

The S-region of HBsAg is of utmost importance and therefore the first region to investigate. The pre-S region of HBsAg is also a possible candidate although there are variants of HBsAg known who do not have a pre-S encoded protein in their virus material (Santantonio et al., 1992, Virology, 188, 948–952). In the same reference, the heterogeneity of HBV pre-S sequences coding for envelope proteins by DNA amplification and direct sequencing of viral genomes is described. In some patients deletions in the pre-S region, mainly clustered at the amino terminal end of the pre-S2 region, were found. The data indicated a high prevalence of HBV genomes that can only express deletion mutants of pre-S2 proteins and most of them cannot express a pre-S2 protein at all. According to the results most of the deletions should not prevent HBs synthesis.

The described heterogeneity of pre-S mutants predicts that false negative results may be obtained when enzyme immunoassays with monoclonal antibodies to pre-S proteins are used solely for their detection in sera of chronic carriers.

It is to the above problem the present invention is addressed.

DETAILED DESCRIPTION OF THE INVENTION

According to the first aspect of the present invention, there is provided a molecule which is capable of specifically binding to a hepatitis B antigen determinant and which either is or cross-competes with a monoclonal antibody directed against at least part of the amino acid sequence:

RDSHPQAMQWNSTTFHQALLDPRVRGLYFPAGGSSSGT (SEQ ID NO: 1).

Preferred fragments comprise at least part of the amino acid sequence:

RDSHPQAMQWNSTTFHQAL (SEQ ID NO: 2), or
SHPQAMQWNSTTFHQALLDPR (SEQ ID NO: 3), or
ALLDPRVRGLYFPAGGSSSGT (SEQ ID NO: 4).

More preferred fragments are MQWN (SEQ ID NO: 5), STRFHQA (SEQ ID NO: 6), or VRGLYFPA (SEQ ID NO: 7), respectively.

A preferred molecule which is capable of specifically binding to a hepatitis B antigen determinant and which either is or cross-competes with a monoclonal antibody secreted by cell line HB.OT104A, HB.OT107C or HB.OT230B. These cell lines have been deposited at the European Collection of Animal Cell Cultures (ECACC), Centre for Applied Microbiology and Research, Salisbury, Wiltshire SP4 OJG, United Kingdom, under the accession numbers ECACC-97062610, ECACC-98042805 or ECACC-97062608, respectively.

Said hepatitis B antigen determinant is located at the pre-S region of HBV.

A specific binding molecule such as an antibody cross-competes with another if it binds to precisely the same, or a conformationally linked, location as the other. Conformationally linked locations may be adjacent locations on the polypeptide chain of the antigen or they may be linked by virtue of the secondary structure of the polypeptide chain, which can cause adjacent folding of otherwise non-adjacent regions. Cross-competition experiments are relatively easy to carry out (Waters et al., 1991). and so it is a straightforward matter to determine whether a given antibody or other specific binding molecule cross-competes with the monocional antibody specifically referred to above.

Specific binding molecules which at least partially cross-compete with the specified monoclonal antibodies (i.e. whose cross-competition is significantly greater than %) are useful in the invention. Specific binding molecules which totally cross-compete (i.e. whose cross-competition is not significantly less than 100%) are preferred, at least in some circumstances.

Specific binding molecules useful in the invention will often themselves be antibodies. While polyclonal antibodies are not excluded, monoclonal antibodies will generally be preferred because of their much more precise specificity. Monoclonal antibody technology has become well established since the original work by Köhler and Milstein (1975, Nature, 256, 495) and there are today many available protocols for the routine generation of monoclonal antibodies. Suitable techniques, for example, are those of Gefter et al., (1977, Somatic Cell Genetics, 3, 231), Köhler et al., (1976, Euro. J. Immuvirol., 292–295) and Goding ("Monoclonal antibodies: Principle and Practice" (2nd Edition, 1986) Academic Press, New York). Typically, the protocol used is as follows:

an experimental animal (such as a mouse) is immunologically challenged with the antigen against which antibodies are to be raised;

the spleen cells of the animal are then fused to cells of a myeloma cell line, and the resultant hybridoma fusion cells plated out on selective medium;

screening for specific antibodies is undertaken by any suitable technique, for example by the use of anti-immunoglobulin antibodies from another species.

While the use of human monoclonal antibodies may in principle be preferred for certain applications, particularly human therapy and in vivo diagnosis, technical difficulties render conventional hybridoma technology inappropriate for the generation of many human monoclonal antibodies. Non-human monoclonal antibodies, such as of murine origin, are therefore often used in practice.

Chimeric antibodies, particularly chimeric monoclonal antibodies, are also included within the scope of the invention. Such chimeric antibodies include sufficient amino acid sequences from HB.OT104A, HB.OT107C; HB.OT230B to have their characteristic specificity. At the minimum, the complementary determining regions of the specified antibody will be present to a sufficient degree to maintain specificity. It may be entire $V_H$ and $V_L$ domains will be present, or even entire antibody binding fragments such as the enzymatically derived Fab or $F(ab')_2$ fragments.

Various different technologies exist for preparing chimeric antibodies. For example, chimeric antibodies consisting of a human C region fused to a rodent V region have been described (Morrison et al., 1984, PNAS, 81, 6851–6855; Boulianne et al., 1984, Nature, 312, 643–646; Neuberger et al., 1985, Nature, 314, 268–270).

Fully humanised antibodies, particularly monoclonal antibodies, are also within the scope of the invention. There are currently three separate methods for humanising non-human (particularly murine) antibodies. Reichmann et al. (!988, Nature, 332, 323–327) used site-directed mutagenesis on ssDNA. In another approach both Jones et al. (1986, Nature, 321, 522–525) and Queen et al. (1989, PNAS, 86, 10029–10033) constructed the whole V region using overlapping oligonucleotides incorporating the rodent complementarity-determining regions (CDRs) on a human framework. More recently, Lewis and Crowe (1991, Gene, 101, 297–302) have adapted polymerase chain reaction (PCR) methodology to graft rodent CDRs onto human immunoglobulin frameworks.

The amino acid sequences of the heavy and light chain variable domains of the monoclonal antibodies can be determined from cloned complementary DNA and the hypervariable regions (or complementarity determining regions CDRs) identified according to Kabat et al. (in "Sequences of Proteins of Immunological Interest", US Department of Health and Human Services, US Government Printing Office, 1987). Using any of the above methods these CDRs can be grafted into a human framework.

The single domain antibodies (dAbs) of Ward et al. (1989, Nature, 341, 544–546), represents another class of specific binding molecules (whether or not they are properly to be regarded. as "antibodies"), which can be used in the scope of the present invention. In this approach, PCR or other appropriate technology is used to clone a $V_H$ or $V_L$ gene and express it in a heterologous host, such as *E. coli.*

The heavy and light chain variable domains can be amplified from the hybridoma using the polymerase chain reaction (PCR) and cloned in expression vectors. The isolated variable domains can be screened for binding to antigen and their affinity determined. Other single domain antibodies can be obtained directly by amplifying by the rearranged variable domain genes from the spleen DNA of an immunised mouse. The amplified DNA can be cloned into a vector and then screened for antigen binding activity. A refinement using bacteriophage as an expression vector allows the phage carrying the variable genes to be selected directly with antigen because they are expressed on the cell surface (McCafferty et al., 1990, Nature, 348, 552–554).

The dabs technology indicates how recombinant DNA methodology is completely changing the generation of molecules having specific binding capabilities. For this reason if no other, the invention should not be regarded as being restricted to antibodies, as understood in the classical sense (whether polyclonal or monoclonal).

According to the second aspect of the present invention, there is provided a cell line or cell culture capable of expressing, and preferably secreting, specific binding molecules as described above.

Within this aspect of the invention are the hybridoma cell lines which have been specifically referred to above. These cell lines have been deposited at the European Collection of Animal Cell Cultures (ECACC), Centre for Applied Microbiology and Research, Salisbury, Wiltshire SP4 OJG, United Kingdom, under the accession numbers and dates shown in the following table:

| Cell line | Deposit date | Accession No. |
|---|---|---|
| HB.OT104A | 26-06-1997 | 97062610 |
| HB.OT107C | 28-04-1998 | 98042805 |
| HB.OT230B | 26-06-1997 | 97062608 |

These deposits have been made under the terms of the Budapest Treaty.

A generalised method for making other monoclonal antibodies has been described above. To ensure that they are within the scope of the invention, a simple cross competition experiment can be reacted with antibodies secreted by the deposited cell line.

Specific antibodies and other binding molecules in accordance with the invention are useful in diagnosis and in therapy.

The above defined antibodies and other binding molecules can be used in diagnostic applications in isolation or in combination with antibodies specifically directed to other regions of the HBV like the S-region.

If used in isolation, another test have to be performed in order to detect the HBV variants which lack the pre-S region.

If used in combination, which is preferred, only one test is necessary. In this instance, the antibodies directed against the S-region, do recognise also the HBV variants which do lack the pre-S region.

The antibodies and other binding molecules according to the present invention do overcome missing HBV infected individuals in the diagnosis of HBV infection.

With these antibodies, the HBsAg test-concept based on the S-region of HBV could be improved. Mutant detection of HBsAg is confirmed.

The antibodies and other binding molecules according to the present invention are useful tools for the detection of HBV expression in cells and cell extracts both in vivo and in vitro, for purification purposes and for a variety of biochemical and immunological analysis techniques to study the function of these proteins.

According to the third aspect of the present invention, there is provided a peptide comprising at least part of the amino acid sequence RDSHPQAMQWNSTTFHQALLD-PRVRGLYFPAGGSSSGT (SEQ ID NO: 1).

A preferred embodiment is a peptide comprising at least part of the amino acid sequence RDSHPQAMQWNSTRF-HQAL (SEQ ID NO: 2). A preferred specific fragment is MQWN (SEQ ID NO: 5).

Another preferred embodiment of a fragment is a peptide comprising at least part of the amino acid sequence SHPQAMQWNSTTFHQALLDPR. (SEQ ID NO: 3) A preferred specific fragment is STFHQA (SEQ ID NO: 6).

Another preferred embodiment of a fragment is a peptide comprising at least part of the amino acid sequence ALL-DPRVRGLYFPAGGSSSGT (SEQ ID. NO: 4). A preferred specific fragment is VRGLYFPA (SEQ ID NO: 7).

Definition of optimal peptides (synthetic or recombinant) representing immunodominant domains of HBsAg, capable of replacing the existing peptides or proteins in diagnostic tests is of crucial importance in order to detect all possible HBsAg positive samples.

These peptides can be synthesized highly reproducible and are easily purified, thus well suited for further improvement and standardization of HBV-serology.

Synthetic peptides have the advantage of being chemically well defined, thus allowing easy and reproducible production at high yields, well suited for application in diagnostic assays which can be manufactured and used with greater reproducibility.

In contrast to natural HBsAg proteins, the peptides according to the present invention have the great advantage that these are of a safe non-infectious origin.

The term "peptide" as used herein refers to a molecular chain of amino acids with a biological activity, and does not refer to a specific length of the product. Thus inter alia, proteins, fusion-proteins or -peptides oligopeptides. and polypeptides are included.

If required peptides according to the invention can be modified in vivo or in vitro, for example by glycosylation, amidation, carboxylation or phosphorylation. Functional variants like, for example, acid addition salts, amides, esters, and specifically C-terminal esters, and N-acyl derivatives of the peptides according to the invention are therefore also considered part of the present invention.

The term "at least a part of" as used herein means a subsequence of the identified amino acid sequence. Said part or fragment is a region having one or more antigenic determinants of the HBsAg proteins. Fragments can inter alia be produced by enzymatic cleavage of precursor molecules, using restriction endonucleases for the DNA and proteases for the (poly)peptides. Other methods include chemical synthesis of the fragments or the expression of peptide fragments by DNA fragments.

The preparation of the peptides or fragments thereof according to the invention is effected by means of one of the known organic chemical methods for peptide synthesis or with the aid of recombinant DNA techniques which are also known in the art. Peptides according to the present invention can also be combined in a single molecule.

As already indicated above, the peptides according to the invention can likewise be prepared with the aid of recombinant DNA techniques. This possibility is of importance particularly when the peptide is incorporated in a repeating sequence ("in tandem") or when the peptide can be prepared as a constituent of a (much larger) protein or polypeptide or as a fusion protein with, for example, (part of) β-galactosidase. This type of peptides therefore likewise falls within the scope of the invention.

The peptides or fragments thereof prepared and described above can also be used to produce antibodies, both polyclonal and monoclonal and other binding molecules.

Methods of diagnosis in accordance with the invention can be carried out in vitro. According to the fourth aspect of the present invention, there is provided a method for the diagnosis of hepatitis B, the method comprising contacting the sample suspected to contain hepatitis B particles or antigens with the specific binding molecule as described above.

A preferred embodiment of the present invention is directed to a method for the diagnosis of hepatitis B, the method comprising contacting the sample suspected to contain hepatitis B particles or antigens with at least one specific binding molecule directed to the S-region of HBV and at least one specific binding molecule according to the present invention.

A particularly suitable method for the detection of HBsAg in a sample is based on a competition reaction between a peptide according to the invention provided with a labeling substance and hepatitis B particles or antigens (present in the sample) whereby the peptide and the antigen are competing with the specific binding molecule according to the present invention attached to a solid support.

Another preferred embodiment of the present invention is directed to a method for the detection of antibodies to hepatitis B, the method comprising contacting the sample suspected to contain antibodies to hepatitis B particles or antigens with at least one peptide according to the present invention.

In in vitro assays, some form of supports are used to immobilise the binding molecules or peptides according to the present invention. Supports which can be used are, for example, the inner wall of a microtest well or a cuvette, a tube or capillary, a membrane, filter, test strip or the surface of a particle such as, for example, a latex particle, an aldehyde particle (such as a ceramic magnetizable particle with active aldehyde surface groups), an erythrocyte, a dye sol, a metal sol or metal compound as sol particle, a carrier protein such as BSA or KLH.

Also some form of labeling is used to detect the antigen-antibody interaction. Labeling substances may be radioactive or non-radioactive such as a radioactive isotope, a fluorescent compound, a chemiluminescent compound, an enzyme, a dye sol, metal sol or metal compound as sol particle. Depending upon the format of the assay, either the specific binding molecules within the scope of the invention can be labeled, or other specific binding molecules, which bind to them are labeled. Immunoassays (including radioimmunoassays) and immunometric assays (including immunometric radloassays and enzyme-linked immunosorbent assays) can be used, as can immunoblotting techniques.

In vitro assays may take many formats. Some depend upon the use of labeled specific binding molecules such as antibodies (whose use is included within the scope of the invention), whereas some detect the interaction of antibody (or other specific binding molecule) and antigen by observing the resulting precipitation. These are well known in the art.

In vitro assays will often be conducted using kits. According to the fifth aspect of the present invention, there is provided an assay kit for the detection of a hepatitis B particle or antigen, the kit comprising a specific binding molecule as described above and means for detecting whether the specific binding molecule is bound to a hepatitis B particle or antigen.

The assay methodology may for example be any of the assays referred to above. Competitive and, especially, sandwich immunoassay kits are preferred. The specific binding molecule and the detection means may be provided in separate compartments of the kit. The specific binding molecule may be provided bound to a solid support. The detections means may comprise a detectable labeled second specific binding molecule (which itself may be an antibody (monoclonal but preferably polyclonal), which bind to the bound hepatitis B particle or antigen.

A preferred embodiment of the present invention to an assay kit for the detection of a hepatitis B particle or antigen, the kit comprising at least one binding molecule directed to the S-region of HBV and at least one specific binding molecule according to the present invention and means for detecting whether the specific binding molecule is bound to a hepatitis B particle or antigen.

Another preferred embodiment of the present invention to an assay kit for the detection of antibodies to hepatitis B, the kit comprising at least one peptide according to the present invention and means for detecting whether the peptide is bound to antibodies to hepatitis B.

Carrying out a sandwich reaction, for the detection of antibodies to hepatitis B the test kit may comprise, for example, a peptide according to the invention coated to a solid support, for example the inner wall of a microtest well, and either a labeled peptide according to the invention or a labeled anti-antibody.

For carrying out a competition reaction, the test kit may comprise a peptide according to the invention coated to a solid support, and a labeled specific binding molecule according to the invention.

According to the sixth aspect of the present invention, there is provided the use of a specific binding molecule according to the present invention for the in vitro diagnosis of hepatitis B. The antibodies and other binding molecules according to the present invention can be useful in the development and quality control of serologic assays and for the direct detection of HBV.

Also the use of the specific binding molecules according to the present invention in immunological and biochemical methods aiming to detect the full length protein in a test fluid or tissue specimen is provided.

The invention is further exemplified by the following examples:

EXAMPLE 1

Production and Selection of (Monoclonal) Antibodies

The murine anti-PreS antibodies HB.OT107C, HB.OT104A and HB.OT230B were produced by injecting Balb/c mice with native-HBsAg in Freund's complete adjuvans. The HBsAg was obtained from sera of HBV infected donors. After two months, mice were boosted with the antigen mixed in Freund's incomplete adjuvans, which was repeated after two weeks. Three days later the spleen was removed and splenic lymphocytes were fused according to CRL manual G6-1 with P3x63Ag8653 (ATCC CRL 1580) mouse myeloma cells using polyethylene glycol 1000 according to standard methods. Hybridoma cells were screened for the production of anti-PreS antibodies using specific peptides and/or denatured HBsAg. Several cycles of cloning by limiting dilution were needed to achieve a stable cell line of 100% clonality.

EXAMPLE 2

Determination of Minimal Evitole of the Antibodies

Materials and methods:

The minimal epitope of HB.OT107C and HB.OT104A was determined by using the standard pepscan method (Geysen et al., 1987, J. Immunol. Meth. 102, 259–274). Peptides based on sequence "MQWNST=HQAL" (SEQ ID NO: 8) were shortened at the N- or C-terminal and tested with HB.OT104A and HBOT107C. Similar experiments were performed with shortened peptides based on sequence "LDPRVRGLYFPA" (SEQ ID NO: 9) and Mab HB.OT230B. For determination of the minimal epitope of HB.OT107C the series was extended with peptides based on sequence "STTHQAL" (SEQ ID NO: 10) shortened at the C-terminal end.

Results:

Results shown in Table 3 indicate that the first methionine (M) at the N-terminus of the Pre-S2 sequence is essential for reactivity of Mab HB.OT104A. The minimal epitope probably includes at least amino acids "MQW". In case of HB.OT107C reactivity declines if the serine (S) or the threonine Cr) at the C-terminus is removed. The epitope of HB.OT107C might include amino acids S (124) and T (126).

TABLE 3

Reactivity of Mab's HB.OT107C and HB.OT104A with peptides based on sequence "120-MQWNSTTFHQAL-131" (SEQ ID NO: 8).

| Sequence | HB.OT 104A | HB.OT. 107C |
|---|---|---|
| MQWNSTTFHQAL (SEQ ID NO: 8) | 2221 | 2890 |
| MQWNSTTFHQA (SEQ ID NO: 11) | 2047 | 2661 |
| MQWNSTTFHQ (SEQ ID NO: 12) | 2135 | 2854 |
| MQWNSTTFH (SEQ ID NO: 13) | 2129 | 2889 |
| MQWNSTTF (SEQ ID NO: 14) | 2218 | 2522 |
| MQWNSTT (SEQ ID NO: 15) | 2441 | 1733 |
| MQWNST (SEQ ID NO: 16) | 1905 | 103 |
| MQWNS (SEQ ID NO: 17) | 2128 | 91 |
| MQWN (SEQ ID NO: 18) | 2188 | 102 |
| MQW | 2013 | 97 |
| MQ | 101 | 83 |
| M | 96 | 82 |
| QWNSTTFHQAL (SEQ ID NO: 19) | 125 | 2639 |
| WNSTTFHQAL (SEQ ID NO: 20) | 124 | 2540 |
| NSTTFHQAL (SEQ ID NO: 21) | 113 | 2612 |
| STTFHQAL (SEQ ID NO: 10) | 112 | 2481 |
| TTFHQAL (SEQ ID NO: 22) | 108 | 88 |
| TFHQAL (SEQ ID NO: 23) | 88 | 82 |
| FHQAL (SEQ ID NO: 24) | 84 | 76 |
| HQAL (SEQ ID NO: 25) | 94 | 83 |
| QAL | 96 | 81 |

TABLE 3-continued

Reactivity of Mab's HB.OT107C and HB.OT104A with peptides based on sequence "120-MQWNSTTFHQAL-131" (SEQ ID NO: 8).

| Sequence | HB.OT 104A | HB.OT. 107C |
|---|---|---|
| AL | 92 | 80 |
| L | 92 | 82 |

The epitope of HB.OT107C was investigated further by using peptides based on sequence "STTFHQAL" (SEQ ID NO: 10). Results are shown in Table 4. The minimal reactive sequence includes amino acids "STTF" (SEQ ID NO: 26). This is in agreement with the results shown in Table 3. The reactivity of sequence "STTFHQA" (SEQ ID NO: 27) is comparable to the reactivity of the original 12-mer peptide "MQWNSTTHQAL" (SEQ ID NO: 8) but if sequence "STTFHQA" (SEQ ID NO: 27) is shortened at the C-terminal side reactivity declines. A very low but measurable reactivity is still obtained found with sequence "STT".

TABLE 4

Minimal epitope mapping of Mab HB.OT107C using peptides based on sequence "124-STTFHQAL-131" (SEQ ID NO: 10).

| Sequence | HB.OT107C |
|---|---|
| MQWNSTTFHQAL (SEQ ID NO: 8) | 2061 |
| NSTTFHQAL (SEQ ID NO: 21) | 2045 |
| STTFHQAL (SEQ ID NO: 22) | 2102 |
| STTFHQA (SEQ ID NO: 27) | 2174 |
| STTFHQ (SEQ ID NO: 28) | 1777 |
| STTFH (SEQ ID NO: 29) | 1757 |
| STTF (SEQ ID NO: 26) | 1626 |
| STT | 327 |
| ST | 97 |
| S | 218 |

In case of HB.OT230B highest reactivity was obtained with the complete 12 mer peptide including sequence "132-LDPRVRGLYFPA-143" (SEQ ID NO: 9). Removal of the alanine (A) at the C-terminus of the peptide results in a strong decrease of reactivity with the antibody. Peptides in which the leucine (L) and/or aspartic acid (D) at the N-terminus is removed still show high reactivity. Elimination of the first proline (P) at the C-terminus, however, strongly decreases the reactivity of the peptide but if both P and the first arginine (A) are removed reactivity increases again. These results are shown in Table 5. Accordingly, the minimal epitope of HB.OT230 probably includes the sequence "VRGLYFPA" (SEQ ID NO: 30).

TABLE 5

Minimal epitope mapping of HB.OT230B based using peptides based on sequence "DPRVRGLYFPA" (SEQ ID NO: 31).

| Sequence | HB.OT 230B |
|---|---|
| DPRVRGLYFPA (SEQ ID NO: 31) | 1753 |
| PRVRGLYFPA (SEQ ID NO: 32) | 1036 |
| RVRGLYFPA (SEQ ID NO: 33) | 650 |
| VRGLYFPA (SEQ ID NO: 30) | 1467 |
| RGLYFPA (SEQ ID NO: 34) | 302 |

TABLE 5-continued

Minimal epitope mapping of HB.OT230B based using peptides based on sequence "DPRVRGLYFPA" (SEQ ID NO: 31).

| Sequence | HB.OT 230B |
|---|---|
| GLYFPA (SEQ ID NO: 35) | 282 |
| LYFPA (SEQ ID NO: 36) | 365 |
| YFPA (SEQ ID NO: 37) | 96 |
| FPA | 77 |
| PA | 80 |
| A | 92 |
| LDPRVRGLYFPA (SEQ ID NO: 9) | 2022 |
| LDPRVRGLYFP (SEQ ID NO: 38) | 208 |
| LDPRVRGLYF (SEQ ID NO: 39) | 103 |
| LDPRVRGLY (SEQ ID NO: 40) | 102 |
| LDPRVRGL (SEQ ID NO: 41) | 90 |
| LDPRVRG (SEQ ID NO: 42) | 87 |
| LDPRVR (SEQ ID NO: 43) | 73 |
| LDPRV (SEQ ID NO: 44) | 88 |
| LDPR (SEQ ID NO: 45) | 78 |
| LDP | 85 |
| LD | 89 |
| L | 88 |

EXAMPLE 3

Replacement of Amino Acids by Alanine (A)

Materials and methods:

In 12-mer peptides reactive with Mab's HB.OT104A and/or HB.OT107C ("MQWNSTTHQAL" (SEQ ID NO: 8) and "STTFHQALLDPR" (SEQ ID NO: 46)) or HB.OT230B ("LDPRVRGLYFPA" (SEQ ID NO: 9)) each amino acid was replaced by an alanine (A). If alanine (A) naturally appeared in the basic sequence it was replaced by serine (S). Reactivity of each peptide was determined by using the standard pepscan technology.

Results:

Results of the ala-study based on peptide "MQWNSTITHQAL" (SEQ ID NO: 8) are shown in Table 6. If the methionine (M) or the tryptophan (W) at the N-terminus was replaced by alanine (A) reactivity of the peptide with Mab HB.OT104A strongly decreased. This finding is in agreement with the epitope mapping results. The minimal epitope of HB.OT104A probably includes the sequence "MQW" but apparently amino acids M(120) and W(122) are most essential for reactivity of the antibody.

Reactivity of HB.OT107C was most sensitive for substitutions considering the serine (S) or phenylalanine (F) located in the middle of the peptide. In all cases, however, reactivity never dropped drastically. According to the epitope mapping both S(124) and F(127) are located in area recognised by HB.OT107C. Results were confirmed in an ala-study based on peptide "124-STTFHQALLDPR-135" (SEQ ID NO: 46) (results are shown in Table 7) but in this case replacement of both amino acids had a more drastic effect on reactivity of the peptide. Both serine (S-124) and the phenylalanine (F-127) seem to be important for reactivity of HB.OT107C.

TABLE 6

Ala-study of HB.OT104A and HB.OT107C. Replacement of each subsequent amino acid in peptide sequence "120-MQWNSTTFHQAL-131" (SEQ ID NO: 8). A-130 is replaced by serine (S).

| Sequence | HB.OT104A | HB.OT107C | amino acid |
|---|---|---|---|
| MQWNSTTFHQAL (SEQ ID NO: 8) | 2198 | 2353 | — |
| AQWNSTTFHQAL (SEQ ID NO: 47) | 460 | 2292 | M |
| MAWNSTTFHQAL (SEQ ID NO: 48) | 1932 | 2281 | Q |
| MQANSTTFHQAL (SEQ ID NO: 49) | 93 | 2224 | W |
| MQWASTTFHQAL (SEQ ID NO: 50) | 2157 | 2501 | N |
| MQWNATTFHQAL (SEQ ID NO: 51) | 1753 | 1679 | S |
| MQWNSATFHQAL (SEQ ID NO: 52) | 2060 | 2319 | T |
| MQWNSTAFHQAL (SEQ ID NO: 53) | 1853 | 1983 | T |
| MQWNSTTAHQAL (SEQ ID NQ: 54) | 2214 | 1601 | F |
| MQWNSTTFAQAL (SEQ ID NO: 55) | 2025 | 2314 | H |
| MQWNSTTFHAAL (SEQ ID NO: 56) | 2264 | 2097 | Q |
| MQWNSTFFHQSL (SEQ ID NO: 57) | 2263 | 2086 | A |
| MQWNSTTFHQAA (SEQ ID NO: 58) | 2138 | 1873 | L |

TABLE 7

Ala-study of HB.OT107C based on peptide "124-STTFHQALLDPR-135" (SEQ ID NO: 46).

| Sequence | HB.OT107C | amino acid |
|---|---|---|
| STTFHQALLDPR (SEQ ID NO: 46) | 2426 | — |
| ATTFHQALLDPR (SEQ ID NO: 59) | 427 | S |
| SATFHQALLDPR (SEQ ID NO: 60) | 1285 | T |
| STAFHQALLDPR (SEQ ID NO: 61) | 1425 | T |
| STTAHQALLDPR (SEQ ID NO: 62) | 220 | F |
| STTFAQALLDPR (SEQ ID NO: 63) | 2279 | H |
| STTFHAALLDPR (SEQ ID NO: 64) | 2342 | Q |
| STTFHQSLLDPR (SEQ ID NO: 65) | 1714 | A |
| STTFHQAALLDPR (SEQ ID NO: 66) | 2058 | L |
| STTFHQALADPR (SEQ ID NO: 67) | 2206 | L |
| STTFHQALLAPR (SEQ ID NO: 68) | 1728 | D |
| STTFHQALLDAR (SEQ ID NO: 69) | 1961 | P |
| STTFHQALLDPA (SEQ ID NO: 70) | 2506 | R |

TABLE 8

Ala-study of HB.OT230B. Each subsequent amino acid in sequence 132-LDPRVRGLYFPA-143 (SEQ ID NO: 9) was replaced by alanine (A). A(143) was replaced by serine (S).

| Sequence | HB.OT230B | amino acid |
|---|---|---|
| LDPRVRGLYFPA (SEQ ID NO: 9) | 2211 | — |
| ADPRVRGLYFPA (SEQ ID NO: 71) | 1408 | L |
| LAPRVRGLYFPA (SEQ ID NO: 72) | 960 | D |
| LDARVRGLYFPA (SEQ ID NO: 73) | 1895 | P |
| LDPAVRGLYFPA (SEQ ID NO: 74) | 1745 | R |
| LDPRARGLYFPA (SEQ ID NO: 75) | 1553 | V |
| LDPRVAGLYFPA (SEQ ID NO: 76) | 2060 | R |
| LDPRVRALYFPA (SEQ ID NO: 77) | 946 | G |
| LDPRVRGAYFPA (SEQ ID NO: 78) | 93 | L |
| LDPRVRGLAFPA (SEQ ID NO: 79) | 157 | Y |

TABLE 8-continued

Ala-study of HB.OT230B. Each subsequent amino acid in sequence 132-LDPRVRGLYFPA-143 (SEQ ID NO: 9) was replaced by alanine (A). A(143) was replaced by serine (S).

| Sequence | HB.OT230B | amino acid |
|---|---|---|
| LDPRVRGLYAPA (SEQ ID NO: 80) | 1155 | F |
| LDPRVRGLYFAA (SEQ ID NO: 81) | 1363 | P |
| LDPRVRGLYFPS (SEQ ID NO: 82) | 1845 | A |

In Table 8 the results of the ala-replacement study considering the reactivity of Mab HB.OT230B are shown. It is clear that replacement of leucined (L-139) or tyrosine (Y-140) had a drastic effect on the reactivity of Mab HB.OT230B. Probably both amino acids are essential for reactivity. According to the mapping results the minimal epitope of HB.OT230B includes amino acids "RGLYFPA" (SEQ ID NO: 83) (see minimal epitope mapping results) but clearly amino acids L(139) and Y(140) are most crucial for reactivity.

EXAMPLE 4

Reactivity of Pre-S2 Antibodies with Peptides Including Naturally Annearing Amino Acid Substitutions Materials and methods:

Various amino acid substitutions were included in peptides based on sequence "MQWNSTRFHQAL" (SEQ ID NO: 8), "STTFHQALLDPR" (SEQ ID NO: 46) or "LDPGVRGLYFPA" (SEQ ID NO: 9). Most substitutions were described previously by Norder et al. (1994) and were based on naturally appearing (subtype) variations within the Pre-S2 region. Peptides were tested with Mab's HB.OT104C and/or HB.OT107C and/or HB.OT230B. Each substitution is mentioned in Tables 9, 10 or 11. The reactivity of each peptide was determined using the standard pepscan technology as already described.

Results:

Based on peptide "MQWNSTTFHQAL" (SEQ ID NO: 8) naturally appearing amino acid substitutions had no. important effect on reactivity of Mab HB.OT104A (see Table 9). In case of HB.OT107C reactivity was affected if the threonine (T-126) at the C-terminus of the peptide was replaced by histidine (H) (see Table 9). Also replacement of C-terminal leucine (L-131) by glutamine (Q) or replacement of arginine (R-135) by glycine (G) resulted in a strongly decrease of reactivity of the peptide.

TABLE 9

Reactivity of peptide "MQWNSTTFHQAL" (SEQ ID NO: 8) with Mab's HB.OT107C and HF.OT104A including naturally occurring amino acid substitutions.

| Sequence | HB.OT104A | HB.OT107C | mutation |
|---|---|---|---|
| MQWNSTTFHQAL (SEQ ID NO: 8) | 2198 | 2098 | |
| MQWTSTTFHQAL (SEQ ID NO: 84) | 2173 | 2343 | N/T |
| MQWNSTAFHQAL (SEQ ID NO: 53) | 1598 | 2241 | T/A |
| MQWNSTHFHQAL (SEQ ID NO: 85) | 2098 | 192 | T/H |
| MQWNSTTLHQAL (SEQ ID NO: 86) | 2456 | 2595 | F/L |
| MQWNSTTFQQAL (SEQ ID NO: 87) | 2621 | 2591 | H/Q |

TABLE 9-continued

Reactivity of peptide "MQWNSTTFHQAL" (SEQ ID NO: 8) with Mab's HB.OT107C and HF.OT104A including naturally occurring amino acid substitutions.

| Sequence | HB.OT104A | HB.OT107C | mutation |
|---|---|---|---|
| MQWNSTTFHQVL (SEQ ID NO: 88) | 1992 | 1926 | A/V |
| MQWNSTTFHQTL (SEQ ID NO: 89) | 2282 | 2332 | A/T |
| MHWNSTTFHQAL (SEQ ID NO: 90) | 1993 | 2071 | Q/H |

TABLE 10

Reactivity of peptide "STTFHQALLDPR" (SEQ ID NO: 46) with Mab HB.OT107C including naturally occurring amino acid substitutions.

| Sequence | HB.OT107C | mutaion |
|---|---|---|
| STTFHQALLDPR (SEQ ID NO: 46) | 2426 | — |
| STTFHQALQDPR (SEQ ID NO: 91) | 83 | L/Q |
| STTFHQALLDPG (SEQ ID NO: 92) | 81 | R/G |

Reactivity of HB.OT230B was affected by replacement of glycine (G-138) by valine (V) and phenylalanine (F-141) by leucine (L). These results are in agreement with the ala-study which showed that replacement of glycine (G-138) by alanine (A) and phenylalanine (F-141) by alanine (A) decreased the reactivity of the peptide.

TABLE 11

Reactivity of peptide "LDPRVRGLYFPA" (SEQ ID NO: 9) with Mab HB.OT230B including naturally occurring amino acids substitutions.

| Sequence | HB.OT230C | mutaion |
|---|---|---|
| LDPRVRGLYFPA (SEQ ID NO: 9) | 2211 | — |
| QDPRVRGLYFPA (SEQ ID NO: 93) | 1876 | L/Q |
| LDPGVRGLYFPA (SEQ ID NO: 94) | 1388 | R/G |
| LDPRVRALYFPA (SEQ ID NO: 77) | 1120 | G/A |
| LDPRVRVLYFPA (SEQ ID NO: 95) | 280 | G/V |
| LDPRVRGLYLPA (SEQ ID NO: 96) | 400 | F/L |
| LDPRVRGLYFPP (SEQ ID NO: 97) | 1591 | A/P |

EXAMPLE 5

Screening HBsAg-mutant Patient Serum

Materials and methods:

One HBsAg-mutant patient serum was used to investigate the sensitivity of immunoassays comprising the binding molecule according to the present invention.

In one assay, called 'basic assay', only murine monoclonal antibodies are used directed to the S-region of HBsAg. In the other assay (which is the assay according to the present invention), called 'improved assay', a murine monoclonal antibody directed to the pre-S region of HBsAg is added to the monoclonal antibodies already present in the basic assay.

Specifically, microelisa wells were coated with said monoclonal antibodies. Each microelisa well contained an HRP-labeled anti-HBs conjugate sphere comprising antibody to HBsAg (anti-HBs) coupled to horseradish peroxidase (HRP) which serves as the conjugate with tetramethylbenzidine (TMB) and peroxide as the substrate.

The test sample or appropriate controls were incubated in the microelisa wells.

The conjugate sphere dissolves in the sample and a solid phase antibody/HBsAg/enzyme-labeled antibody complex is formed. Following a wash and incubation with TMB substrate, color is produced which turns yellow when the reaction is stopped with sulfuric acid. If HBsAg is present in the sample, a color develops. However, when the sample is free of HBsAg, no or low color forms with the addition of substrate. Within limits, the amount of HBsAg in the sample is proportional to the color development.

The sample was tested undiluted.

Both assays (basic—and improved assay) were carried out according the same procedure.

The HBsAg-mutant patient serum is:

Patientserum 1: Mutant 129R/133T.

This sample was a kind gift of Dr. T. Cuijpers (described in Jongerius et al., 1997, Ned Tijdschr Geneesk 141 (22) 1128).

Into each well of both plates 100 μl of culture supernatant or control was pipetted. The plate was covered, agitated for 15 seconds and incubated at 37±2° C. for 1 hour±5 minutes in an OT500 incubator. After incubation the plates were washed four times with phosphate buffer using an OT400 washer. In each well 100 μl TMB substrate was pipetted and incubated at 18–25° C. for 30±2 minutes. Then the reaction was stopped by adding 100 μl 1 M sulftuic acid. After blanking the OT510 reader on air the absorbance of the solution in each well was read at 450±5 nm.

Results:

The results of both assays are listed in Table 12.

For sample 129R/133T the cut off value for the basic assay was 132 and the cut off value for the improved assay was 110.

This sample was negative tested in the basic assay but tested positive in the improved assay.

It is clear that the improved assay was found more reactive when compared with the basic assay.

TABLE 12

Measured absorbance at 450 nm of HBsAg mutant patient serum 129R/133T and negative control tested in the basic assay and the improved assay.

| patient mutant serum | basic assay | pos/neg | improved assay | pos/neg |
|---|---|---|---|---|
| 129R/133T | 94 | neg | 113 | pos |
| blank | 82 | neg | 60 | neg |

neg = negative tested
pos = positive tested
blank = mean of 3 individual wells

EXAMPLE 6

Screening Recombinant HBsAg-mutant Panel

Materials and methods:

Due to the lack of well documented and available HBsAg-mutant patient sera (with the exception of the sample described in example 5), a recombinant HBsAg mutant panel was prepared.

The HBsAg mutant panel was prepared as follows: Both Cos I cells and HepG2 cells were cultured as monolayer in 75 $cm^2$ rouxflasks in 10 ml Dulbecco's MEM medium containing 10% Foetal Calf Serum (FCS) in a 37° C. incubator. Four hours before electroporation the medium was refreshed.

After trypsinisation the cells were diluted in 5 ml medium and 10 minutes 233 g centrifuged in a Beckmann GP centrifuge. For Cos I cell lines $1.5\times10^6$ cells were diluted in 200 μl Phosphate Buffered Saline (PBS), for HepG2 cell lines 5×10[6] cells were diluted in 500 μl medium. Then 20 μl steril DNA solution of each HBsAg recombinant construct was added to the cell suspension. The mixtures were incubated on ice for 5 minutes and pipetted into a 4 mm cuvet. Nine Cos I cells plus DNA combinations were electroporated by 300 V and 125 μF, four HepG2 cells plus DNA combinations were electroplated by 235 V and 960 μF with the Biorad Gene Pulser. Again the mixtures were incubated on ice for 5 minutes. The electroporated cells were diluted in 5 ml medium and cultured in 9 cm dishes in a 37° C. incubator. After about one week of culturing the supernatant was harvested and stored at −20±2° C.

Supernatant derived from 9 Cos I cell lines and 4 HepG2 cell lines were tested in an enzyme-linked immunosorbent assay (ELISA) based on a one-step sandwich principle. Again, the basic assay was compared with the improved assay according to the present invention.

All samples were tested undiluted.

Both assays (basic—and improved assay) were carried out according the same procedure.

Into each well of both plates 100 μl of culture supernatant or control was pipetted. The plate was covered, agitated for 15 seconds and incubated at 37±2° C. for 1 hour±5 minutes in an OT500 incubator. After incubation the plates were washed four times with phosphate buffer using an OT400 washer. In each well 100 μl TMB substrate was pipetted and incubated at 18–25° C. for 30±2 minutes. Then the reaction was stopped by adding 100 μl 1 M sulfuric acid. After blanking the OT510 reader on air the absorbance of the solution in each well was read at 450±5 nm.

Results:

The results of both assays are listed in Table 13.

The constructs, i.e. Cos I cell lines and HepG2 cell lines were tested seperately in two test runs. Run 1: for all the Cos I cell lines the cut off value for the basic assay was 126, the cut off value for the improved assay was 133. Run 2: for the HepG2 cell lines (wildtype and 129/133) the cut off value for the basic assay was 103, the cut off value for the improved assay was 96.

Three samples negative tested in the basic assay were tested positive in the improved assay, i.e. the mutation Cos I 129/145R, Cos I 145R, and HepG2 129/133 were tested negative in the basic assay and positive in the improved assay.

In all cases the improved assay was found more reactive (sensitive) when compared with the basic assay.

TABLE 13

Measured absorbance at 450 nm of 9 Cos I cell lines, 4 HepG2 cell lines and said negative controls tested in the basic assay and the improved assay.

| cell line/ S mutation | basic assay | pos/neg | inproved assay | pos/neg |
|---|---|---|---|---|
| CosI 129 | 1288 | pos | 2377 | pos |
| CosI 129/133 | >3000 | pos | >3000 | pos |
| CosI 129/145R | 115 | neg | 1451 | pos |
| CosI 145A | 1638 | pos | >3000 | pos |
| CosI 145R | 125 | neg | >3000 | pos |
| CosI WT | >3000 | pos | >3000 | pos |
| CosI 129/145A | 1609 | pos | 2717 | pos |
| CosI 133 | 587 | pos | 1456 | pos |
| blank 1 Cos | 94 | neg | 119 | neg |
| HepG2 129/133 | 97 | neg | 105 | pos |
| HepG2 WT | 238 | pos | 425 | pos |
| HepG2 2133 | 110 | pos | 165 | pos |
| HepG2 145A | 231 | pos | 467 | pos |
| blank 2 HepG2 | 68 | neg | 51 | neg |

neg = negative tested
pos = positive tested
WT = wild type

We claim:

1. The cell line HB.OT104A (ECACC 97062610).

2. A monoclonal antibody secreted by a cell line according to claim 1 or an antibody being identical to said monoclonal antibody.

3. A method for the diagnosis of hepatitis B, the method comprising:

(a) contacting the sample suspected to contain hepatitis B particles or antigens with the monoclonal antibody according to claim 2;

(b) detecting whether there is binding between hepatitis B particles or antigens and the monoclonal antibody;

wherein detection of binding between hepatitis B particles or antigens and the monoclonal antibody is diagnostic for the presence of hepatitis B in the sample.

4. An assay kit for the detection of a hepatitis B particle or antigen, the kit comprising a monoclonal antibody according to claim 2 and means for detecting whether the monoclonal antibody is bound to a hepatitis particle or antigen.

5. The cell line HB.OT107C (ECACC 98042805).

6. A monoclonal antibody secreted by a cell line according to claim 5 or an antibody being identical to said monoclonal antibody.

7. A method for the diagnosis of hepatitis B, the method comprising:

(a) contacting the sample suspected to contain hepatitis B particles or antigens with the monoclonal antibody according to claim 5;

(b) detecting whether there is binding between hepatitis B particles or antigens and the monoclonal antibody;

wherein detection of binding between hepatitis B particles or antigens and the monoclonal antibody is diagnostic for the presence of hepatitis B in the sample.

8. An assay kit for the detection of a hepatitis B particle or antigen, the kit comprising a monoclonal antibody according to claim 5 and means for detecting whether the monoclonal antibody is bound to a hepatitis particle or antigen.

9. The cell line HB.OT230B (ECACC 97062608).

10. A monoclonal antibody secreted by a cell line according to claim 9 or an antibody being identical to said monoclonal antibody.

11. A method for the diagnosis of hepatitis B, the method comprising:

(a) contacting the sample suspected to contain hepatitis B particles or antigens with the monoclonal antibody according to claim 10;

(b) detecting whether there is binding between hepatitis B particles or antigens and the monoclonal antibody;

wherein detection of binding between hepatitis B particles or antigens and the monoclonal antibody is diagnostic for the presence of hepatitis B in the sample.

12. An assay kit for the detection of a hepatitis B particle or antigen, the kit comprising a monoclonal antibody according to claim 10 and means for detecting whether the monoclonal antibody is bound to a hepatitis particle or antigen.

* * * * *

UNITED STATES PATENT AND TRADEMARK OFFICE

CERTIFICATE OF CORRECTION

PATENT NO. : 6,541,198 B1 
DATED : April 1, 2003
INVENTOR(S) : Wilhelmina Petronella Paulij et al.

It is certified that error appears in the above-identified patent and that said Letters Patent is hereby corrected as shown below:

<u>Title page,</u>
Item [57], ABSTRACT, please delete the ABSTRACT and insert the following text:

-- The present invention relates to antibodies and other binding molecules specific for hepatitis B viral antigens (HBV), peptides comprising epitopes recognised by such molecules, and cell lines capable of producing antibodies. The invention is further concerned with the use of such molecules in diagnosis of hepatitis B virus (HBV).

The invention further relates to a method for the diagnosis of hepatitis B, the method comprising contacting the sample suspected to contain hepatitis B particles or antigens with the specific binding molecule according to the invention.

More preferred, the invention relates to a method for the diagnosis of hepatitis B, the method comprising contacting the sample suspected to contain hepatitis B particles or antigens with at least one specific binding molecule directed to the S-region of HBV and at least one specific binding molecule according to the present invention.

The invention further relates to an assay kit for the detection of a hepatitis B particle or antigen, the kit comprising a specific binding molecule according to the invention and means for detecting whether the specific binding molecule is bound to a hepatitis B particle or antigen. --

<u>Column 4,</u>
Line 33, should read as follows:
-- STTFHQA (SEQ ID NO: 6), or VRGLYFPA (SEQ ID NO: --

<u>Column 7,</u>
Line 14, should read as follows:
-- part of the amino acid sequence RDSHPQAMQWNSTTF- --
Line 20, should read as follows:
-- ferred specific fragment is STTFHQA (SEQ ID NO: 6). --

Signed and Sealed this

Ninth Day of September, 2003

JAMES E. ROGAN
*Director of the United States Patent and Trademark Office*

SEQUENCE LISTING

```
<160> NUMBER OF SEQ ID NOS: 97

<210> SEQ ID NO 1
<211> LENGTH: 38
<212> TYPE: PRT
<213> ORGANISM: Hepatitis B virus

<400> SEQUENCE: 1

Arg Asp Ser His Pro Gln Ala Met Gln Trp Asn Ser Thr Thr Phe His
1               5                   10                  15

Gln Ala Leu Leu Asp Pro Arg Val Arg Gly Leu Tyr Phe Pro Ala Gly
            20                  25                  30

Gly Ser Ser Ser Gly Thr
        35


<210> SEQ ID NO 2
<211> LENGTH: 19
<212> TYPE: PRT
<213> ORGANISM: Hepatitis B virus
```

-continued

```
<400> SEQUENCE: 2

Arg Asp Ser His Pro Gln Ala Met Gln Trp Asn Ser Thr Thr Phe His
1               5                   10                  15

Gln Ala Leu


<210> SEQ ID NO 3
<211> LENGTH: 21
<212> TYPE: PRT
<213> ORGANISM: Hepatitis B virus

<400> SEQUENCE: 3

Ser His Pro Gln Ala Met Gln Trp Asn Ser Thr Thr Phe His Gln Ala
1               5                   10                  15

Leu Leu Asp Pro Arg
            20


<210> SEQ ID NO 4
<211> LENGTH: 21
<212> TYPE: PRT
<213> ORGANISM: Hepatitis B virus

<400> SEQUENCE: 4

Ala Leu Leu Asp Pro Arg Val Arg Gly Leu Tyr Phe Pro Ala Gly Gly
1               5                   10                  15

Ser Ser Ser Gly Thr
            20


<210> SEQ ID NO 5
<211> LENGTH: 4
<212> TYPE: PRT
<213> ORGANISM: Hepatitis B virus

<400> SEQUENCE: 5

Met Gln Trp Asn
1


<210> SEQ ID NO 6
<211> LENGTH: 7
<212> TYPE: PRT
<213> ORGANISM: Hepatitis B virus

<400> SEQUENCE: 6

Ser Thr Thr Phe His Gln Ala
1               5


<210> SEQ ID NO 7
<211> LENGTH: 8
<212> TYPE: PRT
<213> ORGANISM: Hepatitis B virus

<400> SEQUENCE: 7

Val Arg Gly Leu Tyr Phe Pro Ala
1               5


<210> SEQ ID NO 8
<211> LENGTH: 12
<212> TYPE: PRT
<213> ORGANISM: Hepatitis B virus

<400> SEQUENCE: 8

Met Gln Trp Asn Ser Thr Thr Phe His Gln Ala Leu
1               5                   10
```

-continued

<210> SEQ ID NO 9
<211> LENGTH: 12
<212> TYPE: PRT
<213> ORGANISM: Hepatitis B virus

<400> SEQUENCE: 9

Leu Asp Pro Arg Val Arg Gly Leu Tyr Phe Pro Ala
1 5 10

<210> SEQ ID NO 10
<211> LENGTH: 8
<212> TYPE: PRT
<213> ORGANISM: Hepatitis B virus

<400> SEQUENCE: 10

Ser Thr Thr Phe His Gln Ala Leu
1 5

<210> SEQ ID NO 11
<211> LENGTH: 11
<212> TYPE: PRT
<213> ORGANISM: Hepatitis B virus

<400> SEQUENCE: 11

Met Gln Trp Asn Ser Thr Thr Phe His Gln Ala
1 5 10

<210> SEQ ID NO 12
<211> LENGTH: 10
<212> TYPE: PRT
<213> ORGANISM: Hepatitis B virus

<400> SEQUENCE: 12

Met Gln Trp Asn Ser Thr Thr Phe His Gln
1 5 10

<210> SEQ ID NO 13
<211> LENGTH: 9
<212> TYPE: PRT
<213> ORGANISM: Hepatitis B virus

<400> SEQUENCE: 13

Met Gln Trp Asn Ser Thr Thr Phe His
1 5

<210> SEQ ID NO 14
<211> LENGTH: 8
<212> TYPE: PRT
<213> ORGANISM: Hepatitis B virus

<400> SEQUENCE: 14

Met Gln Trp Asn Ser Thr Thr Phe
1 5

<210> SEQ ID NO 15
<211> LENGTH: 7
<212> TYPE: PRT
<213> ORGANISM: Hepatitis B virus

<400> SEQUENCE: 15

Met Gln Trp Asn Ser Thr Thr
1 5

<210> SEQ ID NO 16

-continued

<211> LENGTH: 6
<212> TYPE: PRT
<213> ORGANISM: Hepatitis B virus

<400> SEQUENCE: 16

Met Gln Trp Asn Ser Thr
1 5

<210> SEQ ID NO 17
<211> LENGTH: 5
<212> TYPE: PRT
<213> ORGANISM: Hepatitis B virus

<400> SEQUENCE: 17

Met Gln Trp Asn Ser
1 5

<210> SEQ ID NO 18
<211> LENGTH: 4
<212> TYPE: PRT
<213> ORGANISM: Hepatitis B virus

<400> SEQUENCE: 18

Met Gln Trp Asn
1

<210> SEQ ID NO 19
<211> LENGTH: 11
<212> TYPE: PRT
<213> ORGANISM: Hepatitis B virus

<400> SEQUENCE: 19

Gln Trp Asn Ser Thr Thr Phe His Gln Ala Leu
1 5 10

<210> SEQ ID NO 20
<211> LENGTH: 10
<212> TYPE: PRT
<213> ORGANISM: Hepatitis B virus

<400> SEQUENCE: 20

Trp Asn Ser Thr Thr Phe His Gln Ala Leu
1 5 10

<210> SEQ ID NO 21
<211> LENGTH: 9
<212> TYPE: PRT
<213> ORGANISM: Hepatitis B virus

<400> SEQUENCE: 21

Asn Ser Thr Thr Phe His Gln Ala Leu
1 5

<210> SEQ ID NO 22
<211> LENGTH: 7
<212> TYPE: PRT
<213> ORGANISM: Hepatitis B virus

<400> SEQUENCE: 22

Thr Thr Phe His Gln Ala Leu
1 5

<210> SEQ ID NO 23
<211> LENGTH: 6
<212> TYPE: PRT

-continued

<213> ORGANISM: Hepatitis B virus

<400> SEQUENCE: 23

Thr Phe His Gln Ala Leu
1 5

<210> SEQ ID NO 24
<211> LENGTH: 5
<212> TYPE: PRT
<213> ORGANISM: Hepatitis B virus

<400> SEQUENCE: 24

Phe His Gln Ala Leu
1 5

<210> SEQ ID NO 25
<211> LENGTH: 4
<212> TYPE: PRT
<213> ORGANISM: Hepatitis B virus

<400> SEQUENCE: 25

His Gln Ala Leu
1

<210> SEQ ID NO 26
<211> LENGTH: 4
<212> TYPE: PRT
<213> ORGANISM: Hepatitis B virus

<400> SEQUENCE: 26

Ser Thr Thr Phe
1

<210> SEQ ID NO 27
<211> LENGTH: 7
<212> TYPE: PRT
<213> ORGANISM: Hepatitis B virus

<400> SEQUENCE: 27

Ser Thr Thr Phe His Gln Ala
1 5

<210> SEQ ID NO 28
<211> LENGTH: 6
<212> TYPE: PRT
<213> ORGANISM: Hepatitis B virus

<400> SEQUENCE: 28

Ser Thr Thr Phe His Gln
1 5

<210> SEQ ID NO 29
<211> LENGTH: 5
<212> TYPE: PRT
<213> ORGANISM: Hepatitis B virus

<400> SEQUENCE: 29

Ser Thr Thr Phe His
1 5

<210> SEQ ID NO 30
<211> LENGTH: 8
<212> TYPE: PRT
<213> ORGANISM: Hepatitis B virus -continued

<400> SEQUENCE: 30

```
Val Arg Gly Leu Tyr Phe Pro Ala
1               5
```

<210> SEQ ID NO 31
<211> LENGTH: 11
<212> TYPE: PRT
<213> ORGANISM: Hepatitis B virus

<400> SEQUENCE: 31

```
Asp Pro Arg Val Arg Gly Leu Tyr Phe Pro Ala
1               5                   10
```

<210> SEQ ID NO 32
<211> LENGTH: 10
<212> TYPE: PRT
<213> ORGANISM: Hepatitis B virus

<400> SEQUENCE: 32

```
Pro Arg Val Arg Gly Leu Tyr Phe Pro Ala
1               5                   10
```

<210> SEQ ID NO 33
<211> LENGTH: 9
<212> TYPE: PRT
<213> ORGANISM: Hepatitis B virus

<400> SEQUENCE: 33

```
Arg Val Arg Gly Leu Tyr Phe Pro Ala
1               5
```

<210> SEQ ID NO 34
<211> LENGTH: 7
<212> TYPE: PRT
<213> ORGANISM: Hepatitis B virus

<400> SEQUENCE: 34

```
Arg Gly Leu Tyr Phe Pro Ala
1               5
```

<210> SEQ ID NO 35
<211> LENGTH: 6
<212> TYPE: PRT
<213> ORGANISM: Hepatitis B virus

<400> SEQUENCE: 35

```
Gly Leu Tyr Phe Pro Ala
1               5
```

<210> SEQ ID NO 36
<211> LENGTH: 5
<212> TYPE: PRT
<213> ORGANISM: Hepatitis B virus

<400> SEQUENCE: 36

```
Leu Tyr Phe Pro Ala
1               5
```

<210> SEQ ID NO 37
<211> LENGTH: 4
<212> TYPE: PRT
<213> ORGANISM: Hepatitis B virus

<400> SEQUENCE: 37

-continued

Tyr Phe Pro Ala
1

<210> SEQ ID NO 38
<211> LENGTH: 11
<212> TYPE: PRT
<213> ORGANISM: Hepatitis B virus

<400> SEQUENCE: 38

Leu Asp Pro Arg Val Arg Gly Leu Tyr Phe Pro
1 5 10

<210> SEQ ID NO 39
<211> LENGTH: 10
<212> TYPE: PRT
<213> ORGANISM: Hepatitis B virus

<400> SEQUENCE: 39

Leu Asp Pro Arg Val Arg Gly Leu Tyr Phe
1 5 10

<210> SEQ ID NO 40
<211> LENGTH: 9
<212> TYPE: PRT
<213> ORGANISM: Hepatitis B virus

<400> SEQUENCE: 40

Leu Asp Pro Arg Val Arg Gly Leu Tyr
1 5

<210> SEQ ID NO 41
<211> LENGTH: 8
<212> TYPE: PRT
<213> ORGANISM: Hepatitis B virus

<400> SEQUENCE: 41

Leu Asp Pro Arg Val Arg Gly Leu
1 5

<210> SEQ ID NO 42
<211> LENGTH: 7
<212> TYPE: PRT
<213> ORGANISM: Hepatitis B virus

<400> SEQUENCE: 42

Leu Asp Pro Arg Val Arg Gly
1 5

<210> SEQ ID NO 43
<211> LENGTH: 6
<212> TYPE: PRT
<213> ORGANISM: Hepatitis B virus

<400> SEQUENCE: 43

Leu Asp Pro Arg Val Arg
1 5

<210> SEQ ID NO 44
<211> LENGTH: 5
<212> TYPE: PRT
<213> ORGANISM: Hepatitis B virus

<400> SEQUENCE: 44

Leu Asp Pro Arg Val
1 5

-continued

<210> SEQ ID NO 45
<211> LENGTH: 4
<212> TYPE: PRT
<213> ORGANISM: Hepatitis B virus

<400> SEQUENCE: 45

Leu Asp Pro Arg
1

<210> SEQ ID NO 46
<211> LENGTH: 12
<212> TYPE: PRT
<213> ORGANISM: Hepatitis B virus

<400> SEQUENCE: 46

Ser Thr Thr Phe His Gln Ala Leu Leu Asp Pro Arg
1 5 10

<210> SEQ ID NO 47
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 47

Ala Gln Trp Asn Ser Thr Thr Phe His Gln Ala Leu
1 5 10

<210> SEQ ID NO 48
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 48

Met Ala Trp Asn Ser Thr Thr Phe His Gln Ala Leu
1 5 10

<210> SEQ ID NO 49
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 49

Met Gln Ala Asn Ser Thr Thr Phe His Gln Ala Leu
1 5 10

<210> SEQ ID NO 50
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 50

Met Gln Trp Ala Ser Thr Thr Phe His Gln Ala Leu
1 5 10

<210> SEQ ID NO 51
<211> LENGTH: 12
<212> TYPE: PRT

-continued

<213> ORGANISM: Artificial sequence
<220> FEATURE:
<223> OTHER INFORMATION: Synthetic polypeptide

<400> SEQUENCE: 51

Met Gln Trp Asn Ala Thr Thr Phe His Gln Ala Leu
1 5 10

<210> SEQ ID NO 52
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 52

Met Gln Trp Asn Ser Ala Thr Phe His Gln Ala Leu
1 5 10

<210> SEQ ID NO 53
<211> LENGTH: 12
<212> TYPE: PRT
<213> ORGANISM: Hepatitis B virus

<400> SEQUENCE: 53

Met Gln Trp Asn Ser Thr Ala Phe His Gln Ala Leu
1 5 10

<210> SEQ ID NO 54
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 54

Met Gln Trp Asn Ser Thr Thr Ala His Gln Ala Leu
1 5 10

<210> SEQ ID NO 55
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 55

Met Gln Trp Asn Ser Thr Thr Phe Ala Gln Ala Leu
1 5 10

<210> SEQ ID NO 56
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 56

Met Gln Trp Asn Ser Thr Thr Phe His Ala Ala Leu
1 5 10

<210> SEQ ID NO 57
<211> LENGTH: 12
<212> TYPE: PRT
<213> ORGANISM: Artificial sequence
<220> FEATURE:
<223> OTHER INFORMATION: Synthetic polypeptide -continued

<400> SEQUENCE: 57

Met Gln Trp Asn Ser Thr Thr Phe His Gln Ser Leu
1 5 10

<210> SEQ ID NO 58
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 58

Met Gln Trp Asn Ser Thr Thr Phe His Gln Ala Ala
1 5 10

<210> SEQ ID NO 59
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 59

Ala Thr Thr Phe His Gln Ala Leu Leu Asp Pro Arg
1 5 10

<210> SEQ ID NO 60
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 60

Ser Ala Thr Phe His Gln Ala Leu Leu Asp Pro Arg
1 5 10

<210> SEQ ID NO 61
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 61

Ser Thr Ala Phe His Gln Ala Leu Leu Asp Pro Arg
1 5 10

<210> SEQ ID NO 62
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 62

Ser Thr Thr Ala His Gln Ala Leu Leu Asp Pro Arg
1 5 10

<210> SEQ ID NO 63
<211> LENGTH: 12
<212> TYPE: PRT
<213> ORGANISM: Artificial sequence
<220> FEATURE:
<223> OTHER INFORMATION: Synthetic polypeptide -continued

<400> SEQUENCE: 63

Ser Thr Thr Phe Ala Gln Ala Leu Leu Asp Pro Arg
1 5 10

<210> SEQ ID NO 64
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 64

Ser Thr Thr Phe His Ala Ala Leu Leu Asp Pro Arg
1 5 10

<210> SEQ ID NO 65
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 65

Ser Thr Thr Phe His Gln Ser Leu Leu Asp Pro Arg
1 5 10

<210> SEQ ID NO 66
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 66

Ser Thr Thr Phe His Gln Ala Ala Leu Asp Pro Arg
1 5 10

<210> SEQ ID NO 67
<211> LENGTH: 12
<212> TYPE: PRT
<213> ORGANISM: Artificial sequence
<220> FEATURE:
<223> OTHER INFORMATION: synthetic polypeptide

<400> SEQUENCE: 67

Ser Thr Thr Phe His Gln Ala Leu Ala Asp Pro Arg
1 5 10

<210> SEQ ID NO 68
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 68

Ser Thr Thr Phe His Gln Ala Leu Leu Ala Pro Arg
1 5 10

<210> SEQ ID NO 69
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 69

-continued

```
Ser Thr Thr Phe His Gln Ala Leu Leu Asp Ala Arg
1               5                   10


<210> SEQ ID NO 70
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 70

Ser Thr Thr Phe His Gln Ala Leu Leu Asp Pro Ala
1               5                   10


<210> SEQ ID NO 71
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 71

Ala Asp Pro Arg Val Arg Gly Leu Tyr Phe Pro Ala
1               5                   10


<210> SEQ ID NO 72
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 72

Leu Ala Pro Arg Val Arg Gly Leu Tyr Phe Pro Ala
1               5                   10


<210> SEQ ID NO 73
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 73

Leu Asp Ala Arg Val Arg Gly Leu Tyr Phe Pro Ala
1               5                   10


<210> SEQ ID NO 74
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 74

Leu Asp Pro Ala Val Arg Gly Leu Tyr Phe Pro Ala
1               5                   10


<210> SEQ ID NO 75
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 75
```

-continued

Leu Asp Pro Arg Ala Arg Gly Leu Tyr Phe Pro Ala
1 5 10

<210> SEQ ID NO 76
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 76

Leu Asp Pro Arg Val Ala Gly Leu Tyr Phe Pro Ala
1 5 10

<210> SEQ ID NO 77
<211> LENGTH: 12
<212> TYPE: PRT
<213> ORGANISM: Hepatitis B virus

<400> SEQUENCE: 77

Leu Asp Pro Arg Val Arg Ala Leu Tyr Phe Pro Ala
1 5 10

<210> SEQ ID NO 78
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 78

Leu Asp Pro Arg Val Arg Gly Ala Tyr Phe Pro Ala
1 5 10

<210> SEQ ID NO 79
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 79

Leu Asp Pro Arg Val Arg Gly Leu Ala Phe Pro Ala
1 5 10

<210> SEQ ID NO 80
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 80

Leu Asp Pro Arg Val Arg Gly Leu Tyr Ala Pro Ala
1 5 10

<210> SEQ ID NO 81
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 81

Leu Asp Pro Arg Val Arg Gly Leu Tyr Phe Ala Ala
1 5 10

-continued

<210> SEQ ID NO 82
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 82

Leu Asp Pro Arg Val Arg Gly Leu Tyr Phe Pro Ser
1 5 10

<210> SEQ ID NO 83
<211> LENGTH: 7
<212> TYPE: PRT
<213> ORGANISM: Hepatitis B virus

<400> SEQUENCE: 83

Arg Gly Leu Tyr Phe Pro Ala
1 5

<210> SEQ ID NO 84
<211> LENGTH: 12
<212> TYPE: PRT
<213> ORGANISM: Hepatitis B virus

<400> SEQUENCE: 84

Met Gln Trp Thr Ser Thr Thr Phe His Gln Ala Leu
1 5 10

<210> SEQ ID NO 85
<211> LENGTH: 12
<212> TYPE: PRT
<213> ORGANISM: Hepatitis B virus

<400> SEQUENCE: 85

Met Gln Trp Asn Ser Thr His Phe His Gln Ala Leu
1 5 10

<210> SEQ ID NO 86
<211> LENGTH: 12
<212> TYPE: PRT
<213> ORGANISM: Hepatitis B virus

<400> SEQUENCE: 86

Met Gln Trp Asn Ser Thr Thr Leu His Gln Ala Leu
1 5 10

<210> SEQ ID NO 87
<211> LENGTH: 12
<212> TYPE: PRT
<213> ORGANISM: Hepatitis B virus

<400> SEQUENCE: 87

Met Gln Trp Asn Ser Thr Thr Phe Gln Gln Ala Leu
1 5 10

<210> SEQ ID NO 88
<211> LENGTH: 12
<212> TYPE: PRT
<213> ORGANISM: Hepatitis B virus

<400> SEQUENCE: 88

Met Gln Trp Asn Ser Thr Thr Phe His Gln Val Leu
1 5 10

-continued

<210> SEQ ID NO 89
<211> LENGTH: 12
<212> TYPE: PRT
<213> ORGANISM: Hepatitis B virus

<400> SEQUENCE: 89

Met Gln Trp Asn Ser Thr Thr Phe His Gln Thr Leu
1 5 10

<210> SEQ ID NO 90
<211> LENGTH: 12
<212> TYPE: PRT
<213> ORGANISM: Hepatitis B virus

<400> SEQUENCE: 90

Met His Trp Asn Ser Thr Thr Phe His Gln Ala Leu
1 5 10

<210> SEQ ID NO 91
<211> LENGTH: 12
<212> TYPE: PRT
<213> ORGANISM: Hepatitis B virus

<400> SEQUENCE: 91

Ser Thr Thr Phe His Gln Ala Leu Gln Asp Pro Arg
1 5 10

<210> SEQ ID NO 92
<211> LENGTH: 12
<212> TYPE: PRT
<213> ORGANISM: Hepatitis B virus

<400> SEQUENCE: 92

Ser Thr Thr Phe His Gln Ala Leu Leu Asp Pro Gly
1 5 10

<210> SEQ ID NO 93
<211> LENGTH: 12
<212> TYPE: PRT
<213> ORGANISM: Hepatitis B virus

<400> SEQUENCE: 93

Gln Asp Pro Arg Val Arg Gly Leu Tyr Phe Pro Ala
1 5 10

<210> SEQ ID NO 94
<211> LENGTH: 12
<212> TYPE: PRT
<213> ORGANISM: Hepatitis B virus

<400> SEQUENCE: 94

Leu Asp Pro Gly Val Arg Gly Leu Tyr Phe Pro Ala
1 5 10

<210> SEQ ID NO 95
<211> LENGTH: 12
<212> TYPE: PRT
<213> ORGANISM: Hepatitis B virus

<400> SEQUENCE: 95

Leu Asp Pro Arg Val Arg Val Leu Tyr Phe Pro Ala
1 5 10

<210> SEQ ID NO 96

-continued

```
<211> LENGTH: 12
<212> TYPE: PRT
<213> ORGANISM: Hepatitis B virus

<400> SEQUENCE: 96

Leu Asp Pro Arg Val Arg Gly Leu Tyr Leu Pro Ala
1               5                   10


<210> SEQ ID NO 97
<211> LENGTH: 12
<212> TYPE: PRT
<213> ORGANISM: Hepatitis B virus

<400> SEQUENCE: 97

Leu Asp Pro Arg Val Arg Gly Leu Tyr Phe Pro Pro
1               5                   10
```